(12) United States Patent

Huang

(10) Patent No.: US 10,117,995 B2
(45) Date of Patent: Nov. 6, 2018

(54) NEEDLE STRUCTURE

(71) Applicant: Hsiang Huang, Taipei (TW)

(72) Inventor: Hsiang Huang, Taipei (TW)

(*) Notice: Subject to any disclaimer, the term of this patent is extended or adjusted under 35 U.S.C. 154(b) by 23 days.

(21) Appl. No.: 15/339,947

(22) Filed: Nov. 1, 2016

(65) Prior Publication Data

US 2017/0312432 A1   Nov. 2, 2017

(30) Foreign Application Priority Data

Apr. 29, 2016 (TW) .............................. 105113497 A
Jun. 24, 2016 (TW) .............................. 105120014 A

(51) Int. Cl.
*A61M 5/19* (2006.01)
*A61M 5/32* (2006.01)
*A61M 5/178* (2006.01)
*A61M 5/31* (2006.01)

(52) U.S. Cl.
CPC ............ *A61M 5/19* (2013.01); *A61M 5/3286* (2013.01); *A61M 5/3297* (2013.01); *A61M 2005/1787* (2013.01); *A61M 2005/3112* (2013.01); *A61M 2209/10* (2013.01)

(58) Field of Classification Search
CPC .... A61M 5/19; A61M 5/3297; A61M 5/3286; A61M 2209/10; A61M 2005/3112; A61M 2005/1787
See application file for complete search history.

(56) References Cited

U.S. PATENT DOCUMENTS

| 6,007,519 A   | * 12/1999 | Rosselli ............ A61M 25/0606 604/164.01 |
| 8,480,645 B1  | * 7/2013  | Choudhury ......... A61M 5/3297 604/405 |
| 2012/0035532 A1 | * 2/2012 | Melsheimer ........ A61M 1/0064 604/28 |

* cited by examiner

*Primary Examiner* — Kevin C Sirmons
*Assistant Examiner* — Amber Stiles
(74) *Attorney, Agent, or Firm* — CKC Partners Co., Ltd.

(57) ABSTRACT

A needle structure for injecting a filler and monitoring a blood backflow situation simultaneously includes a needle, a housing and a partitioning member. The needle includes a needle chamber and a needle opening connected to the needle chamber. The housing includes a housing chamber and a housing opening connected to the housing chamber, and the housing chamber is connected to the needle chamber to form a needle housing chamber. The partitioning member is disposed in the needle housing chamber. The needle housing chamber is separated into a first chamber and a second chamber by the partitioning member. The needle opening is separated into an injection opening and a blood backflow opening by the partitioning member. The first chamber is connected to the injection opening, and the blood backflow opening and the housing opening are connected by the second chamber.

5 Claims, 18 Drawing Sheets

NEEDLE STRUCTURE

RELATED APPLICATIONS

This application claims priority to Taiwan Application Serial Number 105113497, filed Apr. 29, 2016, and Taiwan Application Serial Number 105120014, filed Jun. 24, 2016, which are herein incorporated by reference.

BACKGROUND

Technical Field

The present disclosure relates to a needle structure. More particularly, the present disclosure relates to a needle structure for injecting a filler and monitoring a blood backflow situation simultaneously.

Description of Related Art

In general, when a needle structure is used for injecting a filler (such as hyaluronic acid) into a skin, an injector will exhaust air from a needle chamber of the needle structure before injecting to prevent a bacterial infection caused by an air injection into the body. The filler is put into the needle chamber of the needle by the injector until the needle chamber is fully occupied by the filler. The injector will make sure that there is no air in the needle chamber, and then perform an injection process.

The filler used in medical beauty treatment is high viscous material which is in a semi-solid state. Therefore, if the filler is injected into blood vessels, it will easily cause serious side effects including skin necrosis, blindness, stroke, pulmonary embolism, etc.

Typically, the filler is hypodermically injected. However, when the needle is inserted into a subcutaneous tissue, the injector can not make sure that whether a blood vessel exists in subcutaneous tissue or not for absolutely confirming the accurate injection position of a front end of the needle, so as to be considered as a blind injection. Hence, in practice, the injector should be familiar with an anatomical structure to choose an appropriate injection position. There are two conventional techniques to perform the injection process. One technique is provided to use a blunt needle, and the other technique is provided to perform an aspiration to confirm the blood backflow situation, thus assuring that the needle is not inserted into the blood vessel.

When the aspiration is performed, the injector can confirm the blood backflow situation. However, the fillers based on different materials have different viscosity coefficients. If the filler has higher viscosity coefficient, such as hyaluronic acid, calcium hydroxyapatite (Radiess) or polycaprolactone (PCL, Ellanse), the needle chamber will be fully occupied by the filler having higher viscosity coefficient after exhausting air from the needle chamber. Accordingly, the injector cannot observe the blood backflow situation during the aspiration because the filler's viscosity coefficient is too high to allow the blood refluxing through the needle. If the injector still continues pushing a syringe to inject the filler into the blood vessel, it will cause blood clotting. Therefore, even if the aspiration is performed, using the high viscosity coefficient material as the filler exists a risk of failure in the surgery.

When the blunt needle is used, the front end of the blunt needle has a circular-arc shape, so that the blunt needle does not hurt the blood vessel theoretically. However, if a diameter of the blunt needle is too thin, it still has a certain puncture force similar to the sharp needle, thereby having a certain risk of inserting the blood vessel. In view of the above, no matter what structure of the needle, the conventional techniques have certain dangerous risks because the injector cannot confirm whether or not the needle is inserted into the blood vessel. Therefore, a needle structure for injecting the filler and monitoring the blood backflow situation simultaneously is commercially desirable.

SUMMARY

According to one aspect of the present disclosure, a needle structure for injecting a filler and monitoring a blood backflow situation simultaneously includes a needle, a housing and a partitioning member. The needle includes a needle chamber and a needle opening connected to the needle chamber. The housing is connected to the needle. The housing includes a housing chamber and a housing opening connected to the housing chamber, and the housing chamber is connected to the needle chamber to form a needle housing chamber. The partitioning member is disposed in the needle housing chamber. The needle housing chamber is separated into a first chamber and a second chamber by the partitioning member. The first chamber and the second chamber are separated from each other. The needle opening is separated into an injection opening and a blood backflow opening by the partitioning member. The first chamber is configured to contain the filler and is connected to the injection opening, and the blood backflow opening and the housing opening are connected by the second chamber.

According to another aspect of the present disclosure, a needle structure for injecting a filler and monitoring a blood backflow situation simultaneously includes an inner needle portion and an outer needle portion. The inner needle portion includes a first needle and a first housing. The first needle includes a needle chamber and a needle opening connected to the needle chamber. The first housing is connected to the first needle. The first housing includes a housing chamber connected to the needle chamber to form a first chamber, and the first chamber is configured to contain the filler and is connected to the needle opening. The outer needle portion is disposed around an outside of the inner needle portion. The outer needle portion includes a housing opening and a blood backflow opening. A second chamber is formed between the inner needle portion and the outer needle portion. The first chamber and the second chamber are separated from each other.

According to further another aspect of the present disclosure, a needle structure for injecting a filler and monitoring a blood backflow situation simultaneously includes a needle, a housing and a tube. The needle includes a needle chamber, a needle opening and a partitioning member. The needle opening is connected to the needle chamber. The partitioning member is disposed in the needle chamber. The housing is connected to the needle. The housing includes a housing chamber and a housing opening connected to the housing chamber, and the housing chamber is connected to the needle chamber. The tube has an injection opening and a tube wall. The tube is movably positioned in the housing chamber and the needle chamber. The tube is configured to contain the filler. When a first distance between the partitioning member and the needle opening is smaller than a second distance between the injection opening and the needle opening, the partitioning member and the tube wall are separated to form a blood backflow opening. When the first distance is greater than the second distance, the blood backflow opening is closed by connecting the tube wall to the partitioning member.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
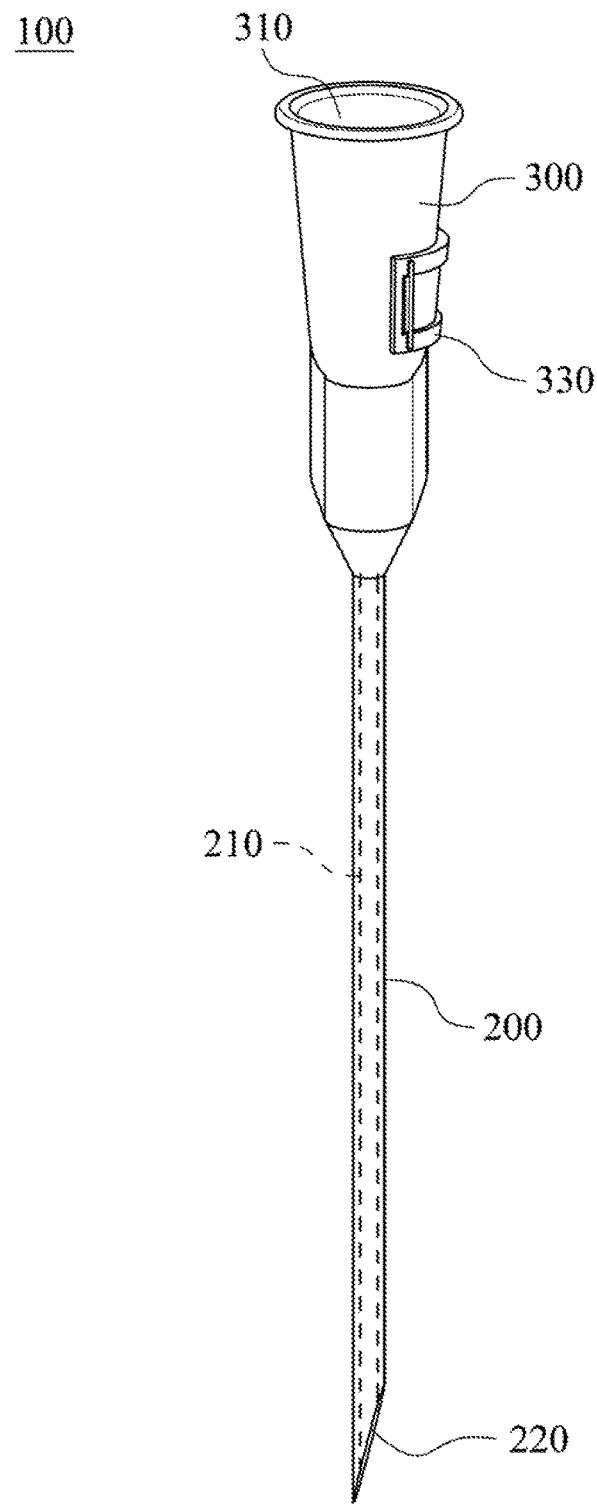
FIG. 1 shows a schematic view of a needle structure according to one embodiment of the present disclosure.
Figure 2:
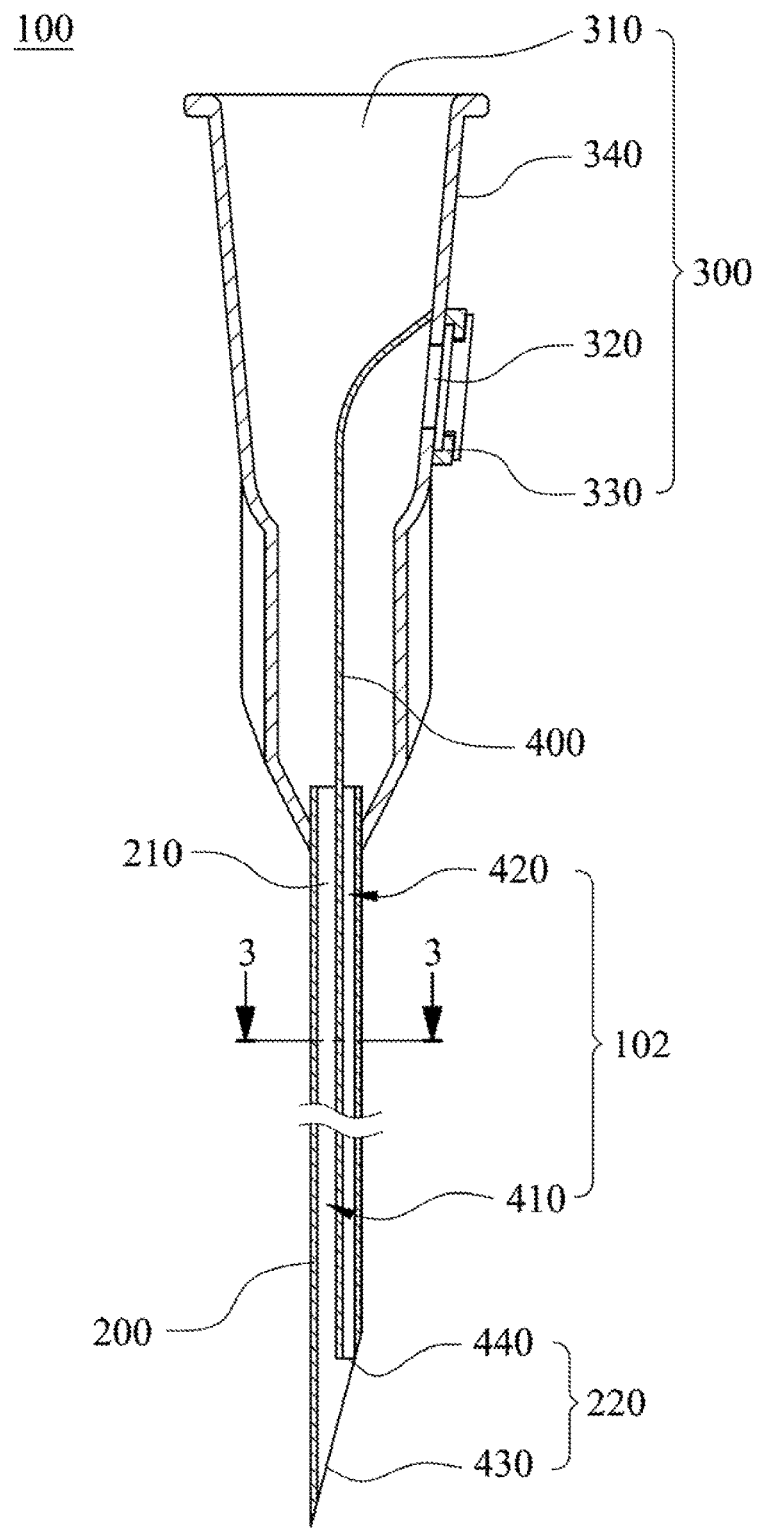
FIG. 2 shows a cross-sectional view of the needle structure of FIG. 1.
Figure 3:
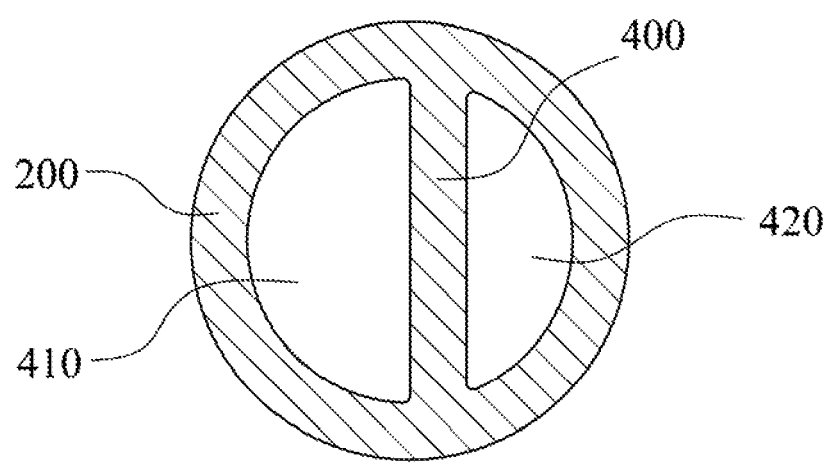
FIG. 3 shows a cross-sectional view of the needle structure taken along line 3-3 of FIG. 2.
Figure 4A:
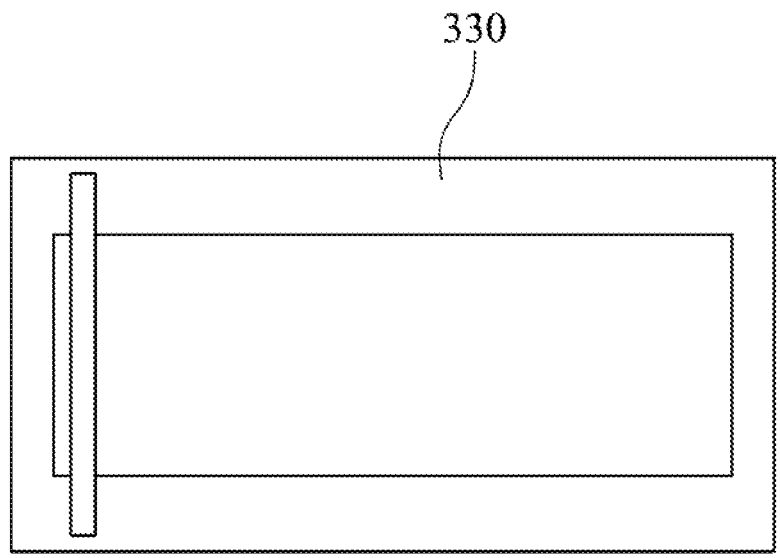
FIG. 4A shows a schematic view of a switch which is closed of FIG. 1.
Figure 4B:
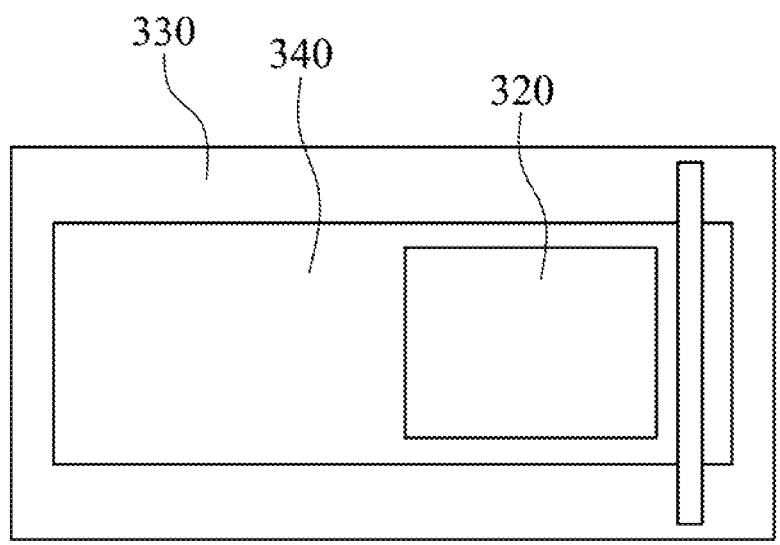
FIG. 4B shows a schematic view of the switch which is opened of FIG. 1.

FIG. 1 shows a schematic view of a needle structure 100 according to one embodiment of the present disclosure; FIG. 2 shows a cross-sectional view of the needle structure 100 of FIG. 1; FIG. 3 shows a cross-sectional view of the needle structure 100 taken along line 3-3 of FIG. 2; FIG. 4A shows a schematic view of a switch 330 which is closed of FIG. 1; and FIG. 4B shows a schematic view of the switch 330 which is opened of FIG. 1. The needle structure is used for injecting a filler. The filler may be hyaluronic acid, calcium hydroxyapatite (Radiess), polycaprolactone (PCL, Ellanse), collagen, poly-L-lactic acid (PLLA), fat, polyacrylamide (PAM), triamcinolone acetonide or lidocaine. Radiess is made of calcium hydroxyapatite, and Ellanse is made of polycaprolactone. These fillers can not be injected into blood vessels. The needle structure 100 is employed for injecting the filler and monitoring a blood backflow situation simultaneously, and can be applied to various medical applications. In other words, the needle structure 100 is used to monitor the blood backflow situation for preventing the filler from being injected into blood vessels. The needle structure 100 includes a needle 200, a housing 300 and a partitioning member 400.

The needle 200 includes a needle chamber 210 and a needle opening 220 connected to the needle chamber 210. The needle 200 may be a blunt needle or a sharp needle. If the needle 200 is the blunt needle, the front end of the needle 200 has a circular-arc shape, and the needle opening 220 is located at the front side of the needle 200. On the other hand, if the needle 200 is the sharp needle, the front end of the needle 200 is beveled or tapered. The needle 200 is an elongated, hollow and cylindrical metal tube, thereby facilitating inserting the front side of the needle 200 into a skin or extracting it from the skin easily.

The housing 300 is connected to the needle 200. The housing 300 includes a housing chamber 310, a housing opening 320, the switch 330 and a housing wall 340. The housing opening 320 is connected to the housing chamber 310, and the housing chamber 310 is connected to the needle chamber 210 to form a needle housing chamber 102. The housing opening 320 is disposed on the housing wall 340. The switch 330 is disposed on the housing opening 320 for opening or closing the housing opening 320. In detail, the switch 330 is corresponding to the housing opening 320 and is disposed on the housing wall 340. The switch 330 is a movable valve for allowing the housing chamber 310 of the housing 300 to communicate with or separate from the outside air. The switch 330 can be manually operated to open or close. Moreover, the housing 300 is made of hard plastic which may be transparent or semi-transparent. In FIG. 2, the housing wall 340 is transparent for allowing an injector to quickly check whether the blood passes through the housing chamber 310 or not.

The partitioning member 400 is disposed in the needle housing chamber 102. The needle housing chamber 102 is separated into a first chamber 410 and a second chamber 420 by the partitioning member 400. The first chamber 410 and the second chamber 420 are separated from each other. The needle opening 220 is separated into an injection opening 430 and a blood backflow opening 440 by the partitioning member 400. The first chamber 410 is configured to contain the filler and is connected to the injection opening 430, and the blood backflow opening 440 and the housing opening 320 are connected by the second chamber 420. In other words, the needle structure 100 of the present disclosure utilizes the partitioning member 400 to divide the needle housing chamber 102 into two chambers which are the first chamber 410 and the second chamber 420, respectively. A size of the first chamber 410 can be equal to, greater than or less than a size of the second chamber 420. In FIG. 2, the size of the first chamber 410 is greater than the size of the second chamber 420. The cross-sectional shapes of the first chamber 410 and the second chamber 420 may be circular, semicircular, oval, rectangular or polygonal.

Figure 5:
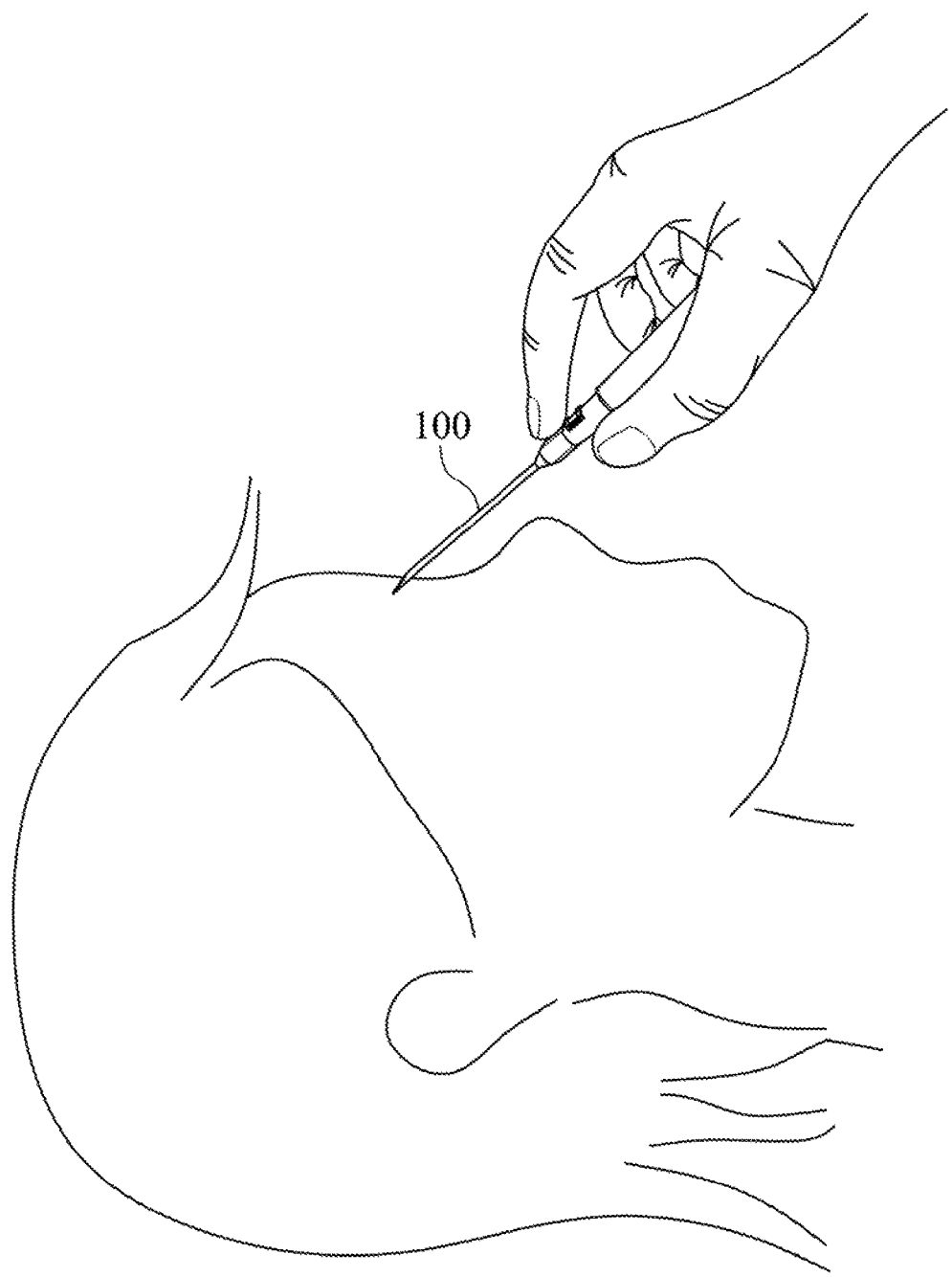
FIG. 5 shows a schematic view of an operation of the needle structure of FIG. 1.

FIG. 5 shows a schematic view of an operation of the needle structure 100 of FIG. 1. The first chamber 410 of the needle structure 100 contains the filler, and the second chamber 420 is configured to monitor the blood backflow situation. The operation of the needle structure 100 can be divided into two steps. One is an inserting step which is for inserting the needle 200 into the skin of a patient by an injector (i.e. a physician or a medical personnel). The other is an injecting step which is for injecting the filler into a non-vascular tissue.

In the inserting step, the injector uses the second chamber 420 to confirm the blood backflow situation. The principle utilized in the present disclosure is a capillary phenomenon of the second chamber 420 as well as a blood pressure inside the blood vessel. If the needle opening 220 is inserted into the blood vessel, the blood will flow through the second chamber 420 to the housing opening 320. Due to the transparent housing wall 340 adjacent to the housing opening 320, the injector can quickly check whether the blood passes through the housing chamber 310 or not. It is similar to a general blood-sucking situation. In order to confirm whether the needle is inserted into the blood vessel or not, a phlebotomist (or a physician) may monitor the blood backflow situation via the hard plastic housing 300. This is because that there is a certain blood pressure inside the blood vessel, and an air inside the needle can be pushed out of the housing 300 by the blood pressure, thereby facilitating the blood flowing through the housing 300. The second chamber 420 of the present disclosure has features that the air is disposed inside the second chamber 420 and disconnected to the filler contained in the first chamber 410, so that the first chamber 410 and the second chamber 420 are both independent spaces. When the filler is injected, the second chamber 420 maintains atmospheric pressure. However, if the front side of the needle 200 is inserted into the blood vessel, the injector can monitor the blood backflow situation via the hard plastic housing 300 because of the capillary phenomenon and the blood pressure. As compared to conventional needle structures, the needle structure 100 of the present disclosure can confirm whether the needle is inserted into the blood vessel or not without the operation of blood-sucking. Thus, the injector can confirm that the needle is not inserted into the blood vessel when there is no blood backflow situation in the inserting step. Therefore, the injector can use the needle structure 100 to safely inject the filler without the operation of blood-sucking, thereby not only increasing the safety of surgery, but also avoiding unnecessary medical disputes. Before the inserting step, the injector needs to open the switch 330 of the housing 300 so as to maintain atmospheric pressure in the second chamber 420. Once the needle tip is inserted into the blood vessel, the injector may see the blood backflow situation and stop injection immediately. When an injection position is determined by the injector and the needle is not moved, the switch 330 of the housing 300 is closed by the injector and then performing the injecting step.

In the injecting step, the filler is injected into the non-vascular tissue. If the injector knows that the front end of the needle 200 is not disposed in the blood vessel, the injector can push a syringe to inject the filler into the non-vascular tissue smoothly. In addition, the switch 330 of the housing 300 is closed for reserving the air in the second chamber 420 and maintaining the constant air pressure of the second chamber 420 in the injecting step, thereby preventing the filler contained in the first chamber 410 from flowing to the second chamber 420. Thus, the space of the second chamber 420 is kept without being blocked by the filler. Furthermore, the filler is often required to perform a multi-point injection. In other words, after extracting the needle structure 100 from the skin, the needle structure 100 can be repeatedly used for the next treatment position by the injector. The injector may open the switch 330, and then a second chamber 420 can be used for monitoring the blood backflow situation. Therefore, when the front side of the needle 200 is inserted into the skin by the injector, the needle structure 100 of the present disclosure can confirm whether the needle 200 is inserted into the blood vessel or not without the operation of blood-sucking, so that the injector can confirm that the needle 200 is not inserted into the blood vessel according to the blood backflow situation. Hence, the needle structure 100 can prevent the filler into the blood vessel from blood clotting, thereby increasing the safety of surgery.

Figure 6:
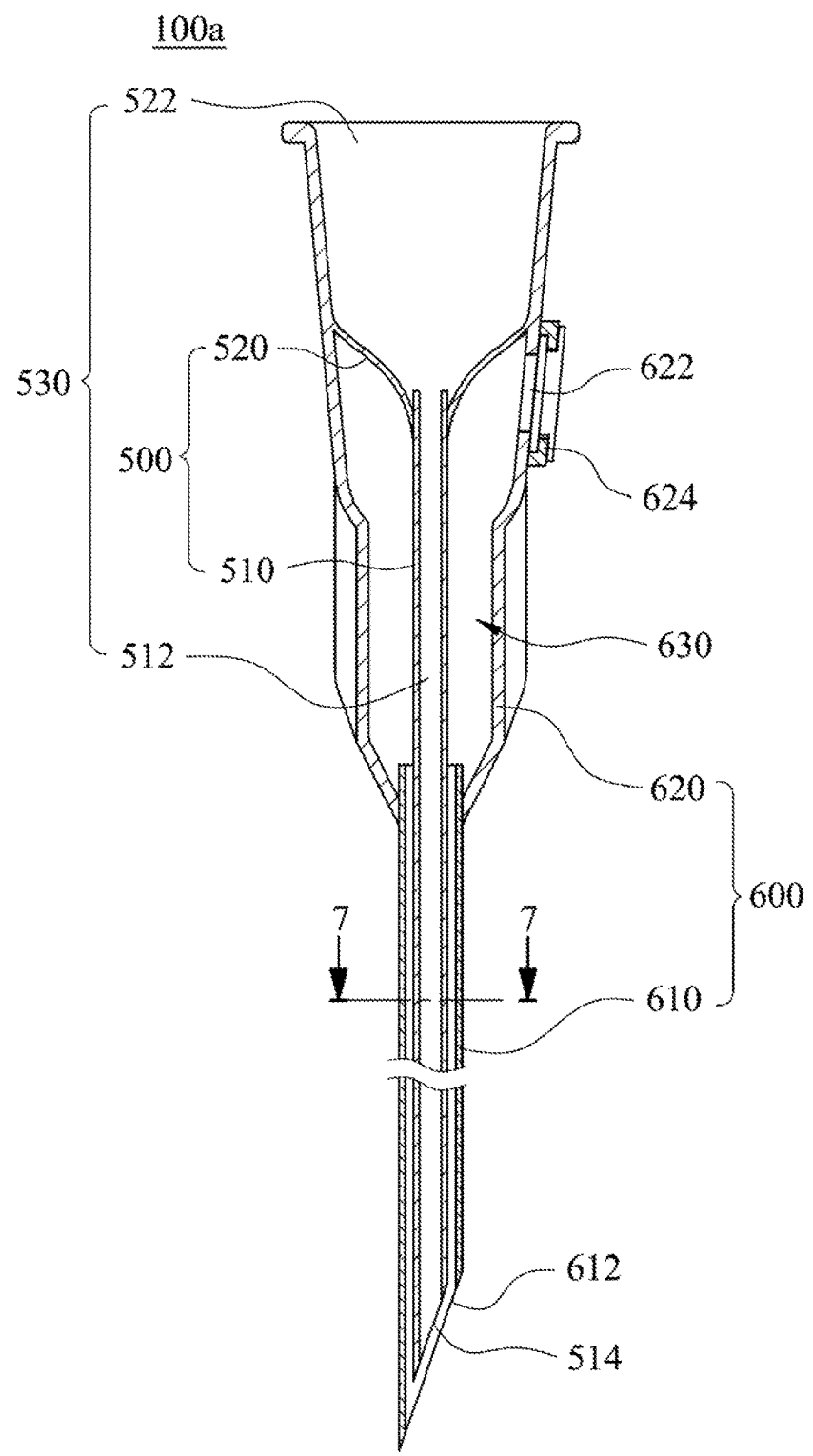
FIG. 6 shows a schematic view of a needle structure according to another embodiment of the present disclosure.
Figure 7:
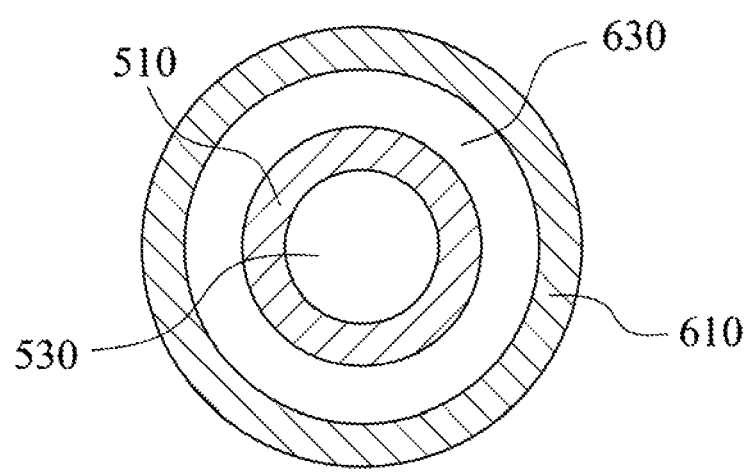
FIG. 7 shows a cross-sectional view of the needle structure taken along line 7-7 of FIG. 6.

FIG. 6 shows a schematic view of a needle structure 100a according to another embodiment of the present disclosure; and FIG. 7 shows a cross-sectional view of the needle structure 100a taken along line 7-7 of FIG. 6. The needle structure 100a for injecting the filler and monitoring the blood backflow situation simultaneously includes an inner needle portion 500 and an outer needle portion 600.

The inner needle portion 500 includes a first needle 510 and a first housing 520. The first needle 510 includes a needle chamber 512 and a needle opening 514 connected to the needle chamber 512. The first housing 520 is connected to the first needle 510. The first housing 520 includes a housing chamber 522 connected to the needle chamber 512 to form a first chamber 530, and the first chamber 530 is configured to contain the filler and is connected to the needle opening 514.

The outer needle portion 600 is disposed around an outside of the inner needle portion 500. The outer needle portion 600 includes a second needle 610, a second housing 620, a housing opening 622, a blood backflow opening 612 and a switch 624. The second needle 610 is disposed around an outside of the first needle 510. The blood backflow opening 612 is disposed on the second needle 610. The second housing 620 is connected to the second needle 610 and is disposed around an outside of the first housing 520, and the housing opening 622 and the switch 624 are both disposed on the second housing 620. Moreover, a second chamber 630 is formed between the inner needle portion 500 and the outer needle portion 600. The first chamber 530 and the second chamber 630 are separated from each other, and the blood backflow opening 612 and the housing opening 622 are connected by the second chamber 630. In FIG. 6, the detail of the switch 624 is the same as the embodiments of FIG. 4A and FIG. 4B, and will not be described again herein. The second housing 620 is made of hard plastic which may be transparent or semi-transparent. In FIG. 6, the second housing 620 is transparent for allowing the injector to quickly check whether the blood passes through the second chamber 630 or not. Therefore, the special annular structure of the second chamber 630 of the needle structure 100a of the present disclosure between the inner needle portion 500 and the outer needle portion 600 can be employed to confirm the blood backflow situation and prevent the filler into the blood vessel from blood clotting, thereby substantially increasing the safety of surgery.

Figure 8:
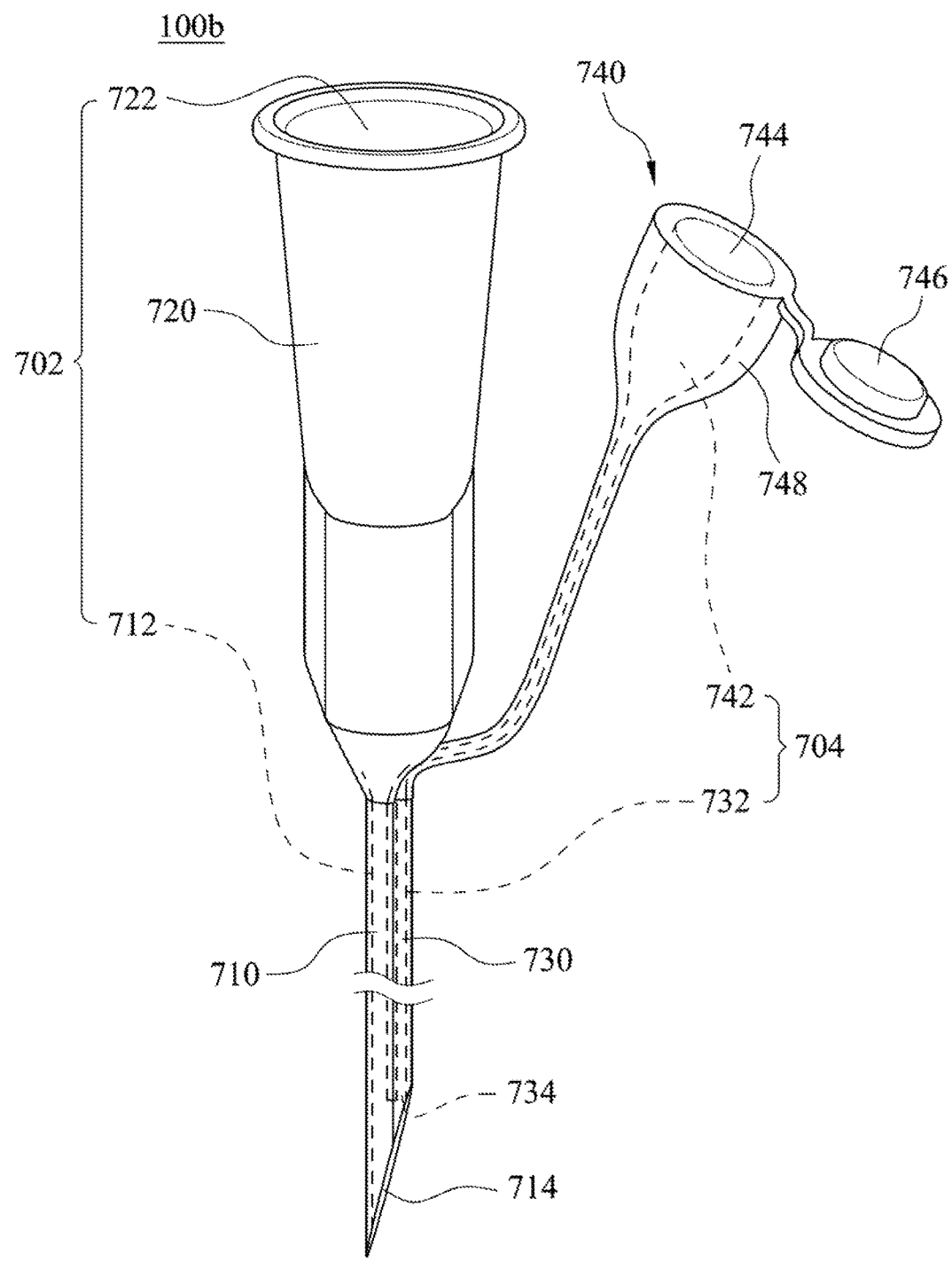
FIG. 8 shows a schematic view of a needle structure according to further another embodiment of the present disclosure.

FIG. 8 shows a schematic view of a needle structure 100b according to further another embodiment of the present disclosure. The needle structure 100b includes a first needle 710, a first housing 720, a second needle 730 and a second housing 740. The first needle 710 includes a first needle chamber 712 and an injection opening 714. The first needle chamber 712 is connected to the injection opening 714. The cross-sectional shape of the first needle chamber 712 may be circular, semicircular, oval, rectangular or polygonal. The first housing 720 is connected to the first needle 710 and includes a first housing chamber 722. The first needle chamber 712 is connected to the first housing chamber 722 to form a first chamber 702. The second needle 730 is compactly connected to the first needle 710, and its cross-sectional shape may be circular, semicircular, oval, rectangular or polygonal. The second needle 730 includes a second needle chamber 732 and a blood backflow opening 734 connected to the second needle chamber 732. The blood backflow opening 734 is adjacent to the injection opening 714. The second housing 740 is connected to the second needle 730. The second housing 740 includes a second housing chamber 742, a housing opening 744, a switch 746 and a housing wall 748. The second needle chamber 732 is connected to the second housing chamber 742 to form a second chamber 704. The first chamber 702 and the second chamber 704 are separated from each other. The first chamber 702 is configured to contain the filler, and the blood backflow opening 734 and the housing opening 744 are connected by the second chamber 704. The switch 746 is disposed on the housing wall 748 for opening or closing the housing opening 744. The housing wall 748 of the second housing 740 is transparent for allowing the injector to quickly check whether the blood passes through the second chamber 704 or not. In FIG. 8, the switch 746 is a cover and is pivotally connected to the housing wall 748. When the switch 746 is put on the housing wall 748, the housing opening 744 is closed by the switch 746, and the second chamber 704 and the outside air are separated from each other. The switch 746 can be manually operated to open or close. In addition, one end of the second needle 730 has a curved shape. In detail, the second housing 740 adjacent to the second needle 730 has a curved shape, so that there is an angle between an extending direction of the first housing 720 and an extending direction of the second housing 740. The angle may be greater than 10 degrees and smaller than 90 degrees. In FIG. 8, the angle is 45 degrees for disposing a sufficient operating space. If the angle is too small, the first housing 720 and the second housing 740 will be too close to easily operate the switch 746. Therefore, the needle structure 100b of the present disclosure not only can confirm the blood backflow situation without the operation of blood-sucking to increasing the safety of surgery, but also can improve the convenience of operation, thereby accomplishing the injection process successfully.

Figure 9:
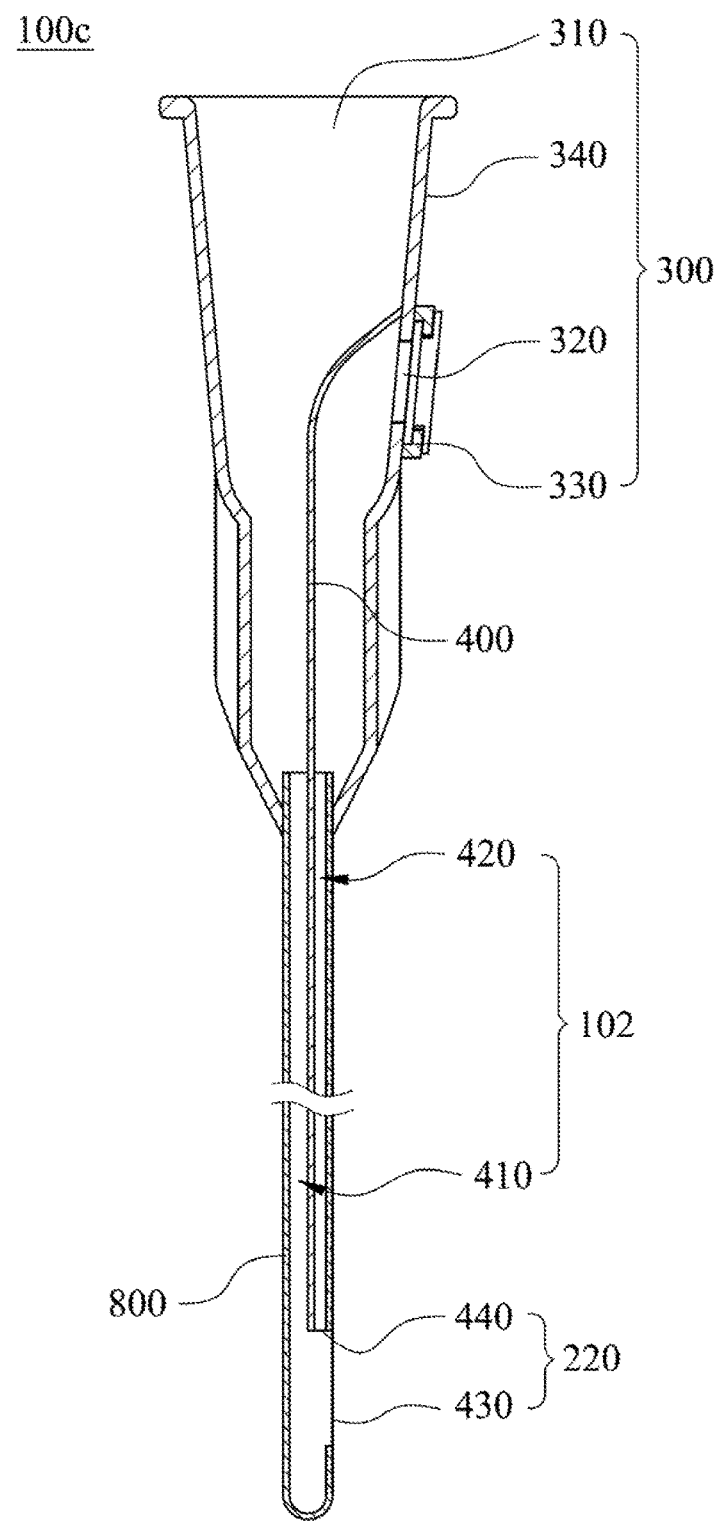
FIG. 9 shows a schematic view of a needle structure according to still further another embodiment of the present disclosure.

FIG. 9 shows a schematic view of a needle structure 100c according to still further another embodiment of the present disclosure. The needle structure 100c includes a needle 800, a housing 300 and a partitioning member 400. In FIG. 9, the detail of the housing 300 and the partitioning member 400 is the same as the embodiments of FIG. 2, and will not be described again herein. In FIG. 9, the needle 800 is a blunt needle, and the front end of the needle 800 has a circular-arc shape. The partitioning member 400 is disposed in the needle housing chamber 102. The needle housing chamber 102 is separated into a first chamber 410 and a second chamber 420 by the partitioning member 400. The first chamber 410 and the second chamber 420 are separated from each other. The needle opening 220 is separated into an injection opening 430 and a blood backflow opening 440 by the partitioning member 400. The first chamber 410 is configured to contain the filler and is connected to the injection opening 430, and the blood backflow opening 440 and the housing opening 320 are connected by the second chamber 420. Due to the needle opening 220 located at the front side of the needle 800, the injection opening 430 and the blood backflow opening 440 are both located at the front side of the needle 800. Furthermore, the front end of the partitioning member 400 near to the needle opening 220 and the injection opening 430 are separated by a distance, thereby injecting the filler and monitoring the blood backflow situation simultaneously. On the contrary, if the front end of the partitioning member 400 is aligned with the injection opening 430 (i.e. the distance is equal to zero), the injection opening 430 may be located inside the blood vessel and the blood backflow opening 440 may be located outside the blood vessel when the needle structure 100c is operated by the injector, thereby generating blood clotting. In FIG. 9, the distance is greater than zero, and the needle structure 100c can avoid blood clotting. Therefore, the needle structure 100c has the first chamber 410 and the second chamber 420 disconnected to the first chamber 410. The first chamber 410 is configured to contain the filler. The second chamber 420 is transparent, and the housing 300 has the housing opening 320 and the switch 330 for confirming the blood backflow situation. When the housing opening 320 is opened, the housing 300 can be used to check the blood backflow situation. When the housing opening 320 is closed, the filler is not entered into the second chamber 420. The structure of the needle structure 100c can prevent the filler into the blood vessel from blood clotting, thereby increasing the safety of surgery.

Figure 10A:
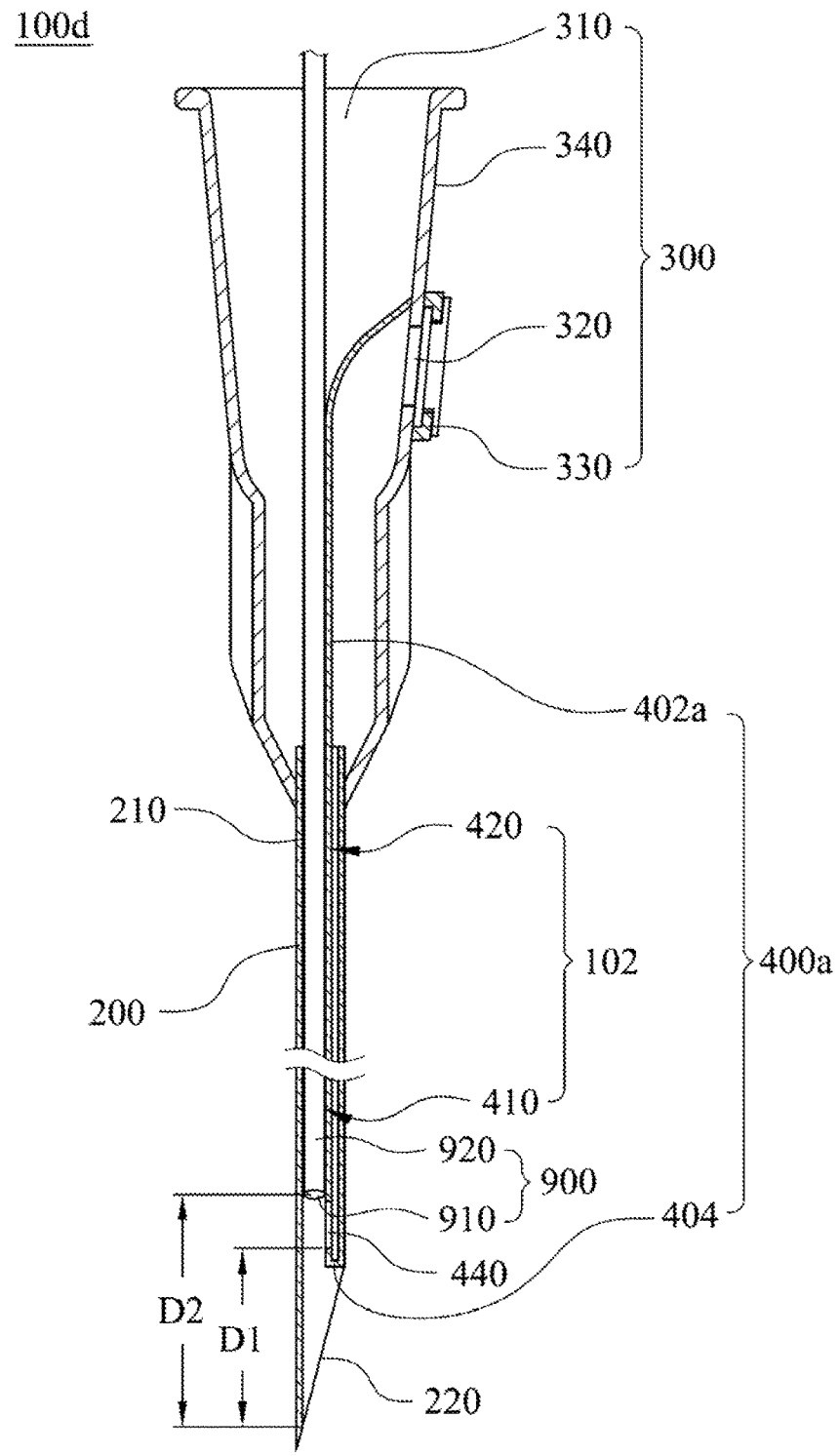
FIG. 10A shows a schematic view of a needle structure for monitoring a blood backflow situation according to another embodiment of the present disclosure.
Figure 10B:
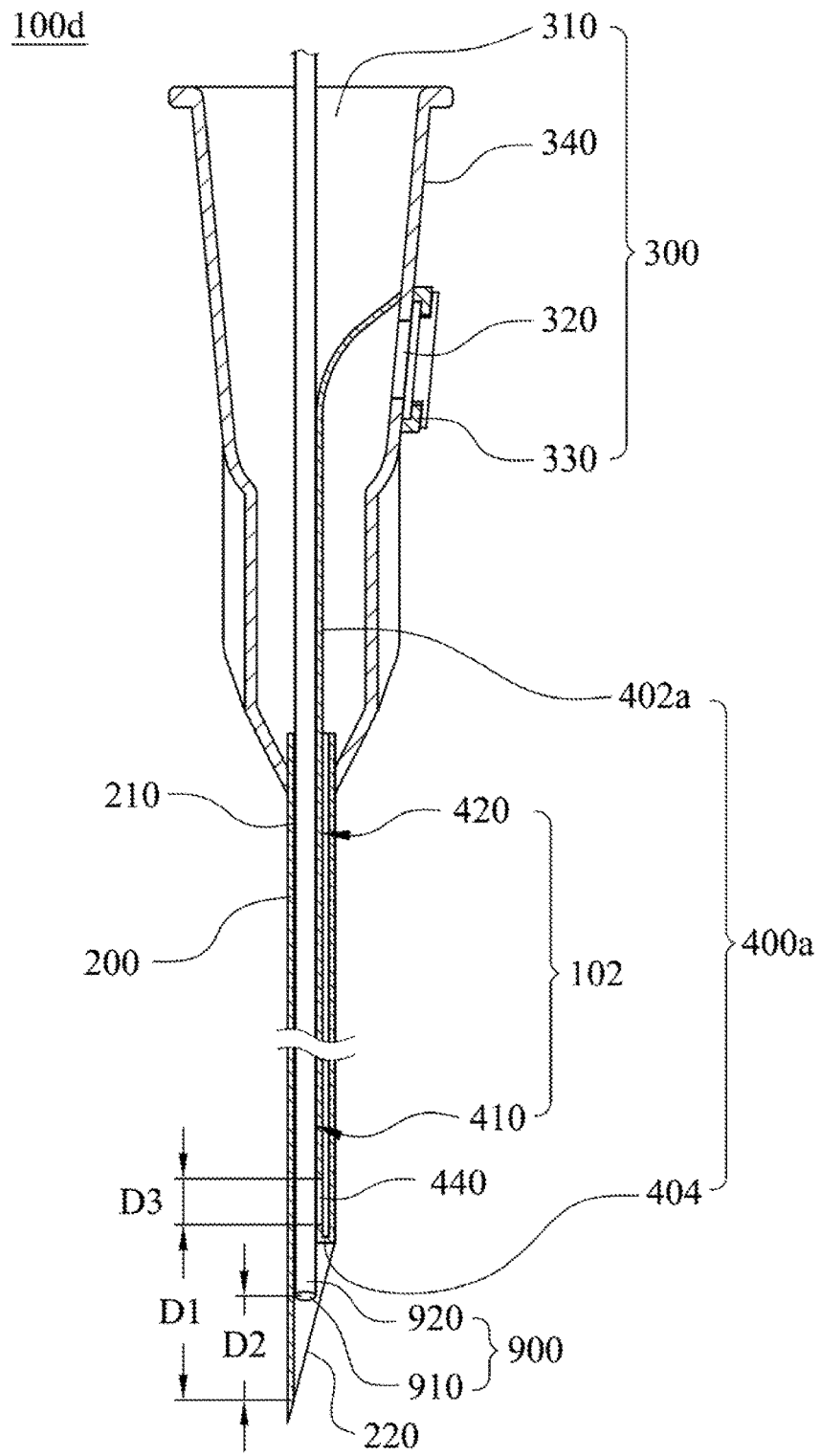
FIG. 10B shows a schematic view of the needle structure for injecting a filler of FIG. 10A.

FIG. 10A shows a schematic view of a needle structure 100d for monitoring the blood backflow situation according to another embodiment of the present disclosure; and FIG. 10B shows a schematic view of the needle structure 100d for injecting the filler of FIG. 10A. The needle structure 100d includes a needle 200, a housing 300, a partitioning member 400a and a tube 900. The needle 200 is a sharp needle. In FIGS. 10A and 10B, the detail of the needle 200 and the housing 300 is the same as the embodiments of FIG. 2, and will not be described again herein. In FIGS. 10A and 10B, the needle structure 100d further includes the partitioning member 400a and the tube 900. The partitioning member 400a is disposed in the needle housing chamber 102, and includes a first partitioning portion 402a, a second partitioning portion 404 and a blood backflow opening 440. The needle housing chamber 102 is separated into a first chamber 410 and a second chamber 420 by the partitioning member 400a. The first chamber 410 is connected to the second chamber 420 by the blood backflow opening 440 adjacent to the needle opening 220. The blood backflow opening 440 is located between the first partitioning portion 402a and the second partitioning portion 404. The blood backflow opening 440 has a diameter D3. One end of the first partitioning portion 402a is connected to an inner wall of the needle 200, and the other end of the first partitioning portion 402a is connected to an inner edge of the housing wall 340. The second partitioning portion 404 is disposed in the needle chamber 210 and has a L-shape in side view. In detail, the blood backflow opening 440 and the housing opening 320 are connected by the second chamber 420, so that the second chamber 420 is located between the blood backflow opening 440 and the housing opening 320. The blood backflow opening 440 and the needle opening 220 are separated by a first distance D1. In addition, the tube 900 has an injection opening 910 and a tube wall 920. The tube 900 is movably positioned in the first chamber 410 and configured to contain the filler. The shape of the tube wall 920 is equal to the shape of the first chamber 410. The operation of the needle structure 100d can be divided into two steps. The first step is for confirming the blood backflow situation, and the second step is for injecting the filler. In the first step, the injector penetrates the tube 900 through the first chamber 410 and moves the injection opening 910 to a first position, so that a second distance D2 between the injection opening 910 and the needle opening 220 is greater than the first distance D1. The second chamber 420 is communicated with the needle opening 220, so that the injector can confirm whether the needle 200 is inserted into the blood vessel or not according to the blood backflow situation, as shown in FIG. 10A. In the second step, the injector pushes the tube 900 an interval toward the needle opening 220, so that the second distance D2 is smaller than the first distance D1. When the first distance D1 is greater than the second distance D2, the blood backflow opening 440 is closed by the tube wall 920 of the tube 900 so as to separate the second chamber 420 from the first chamber 410, as shown in FIG. 10B. After that, the injector injects the filler disposed in the tube 900 to the needle opening 220 and then extracts the tube 900 from the needle 200 to complete the injection process. The needle structure 100d can prevent the filler into the second chamber 420 from plugging, thus decreasing the difficulty of cleaning. Moreover, after the injection process, the tube 900 can be pulled out of the first chamber 410 and discarded, and the needle 200 can be recycled after cleaning. Another tube 900 contained with the filler may be pushed into the needle 200 for the next injection process so as to reduce the manufacturing cost, enhance the convenience of operation and increase the operation safety. Due to a high viscous material of the filler, the conventional needle structure can not be used when an obstruction is caused by the filler in the needle. However, the needle structure 100d of the present disclosure not only can allow the injector to successfully accomplish the injection process, but also can greatly reduce the occurrence of side effects and accidents.

Figure 11A:
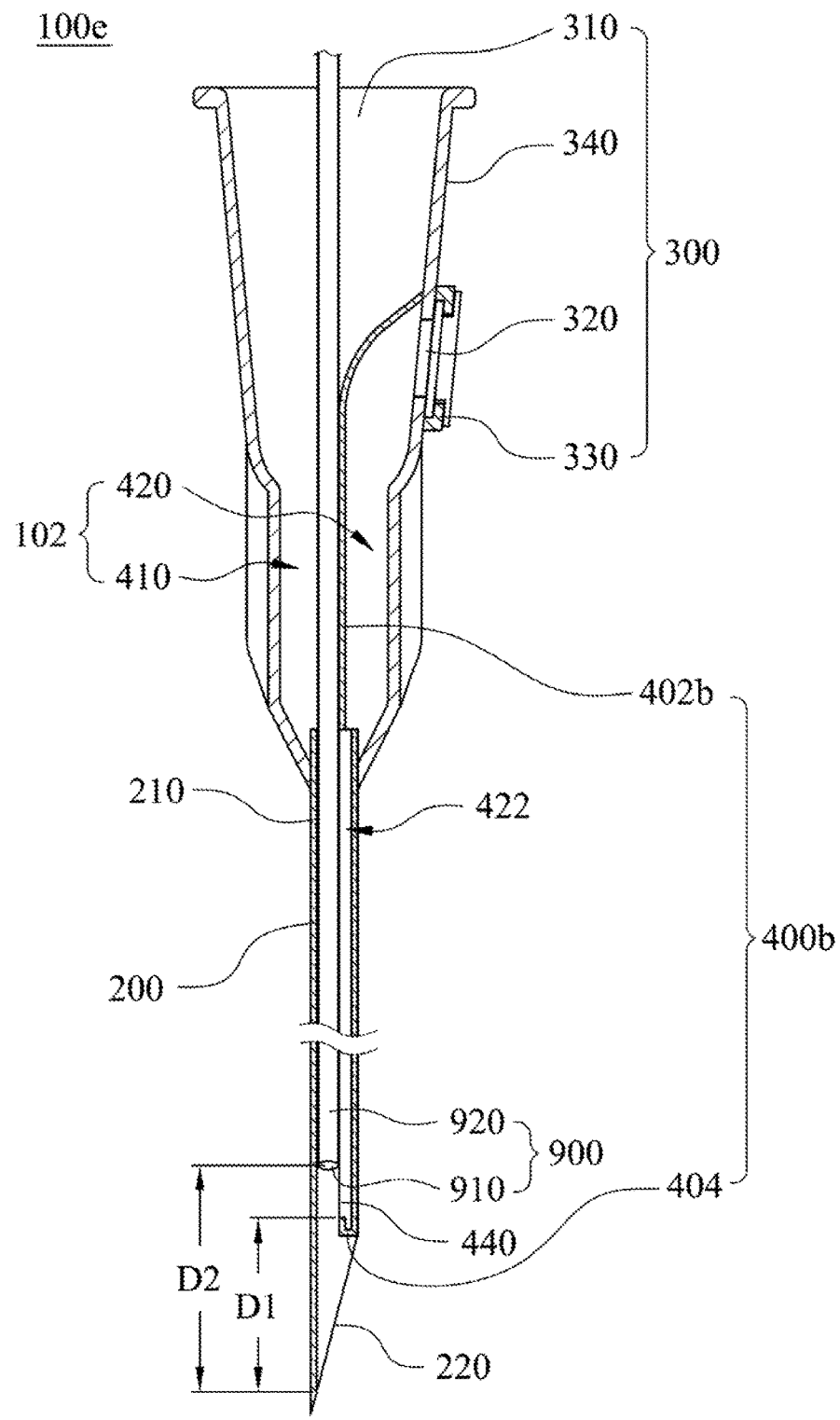
FIG. 11A shows a schematic view of a needle structure for monitoring a blood backflow situation according to further another embodiment of the present disclosure.
Figure 11B:
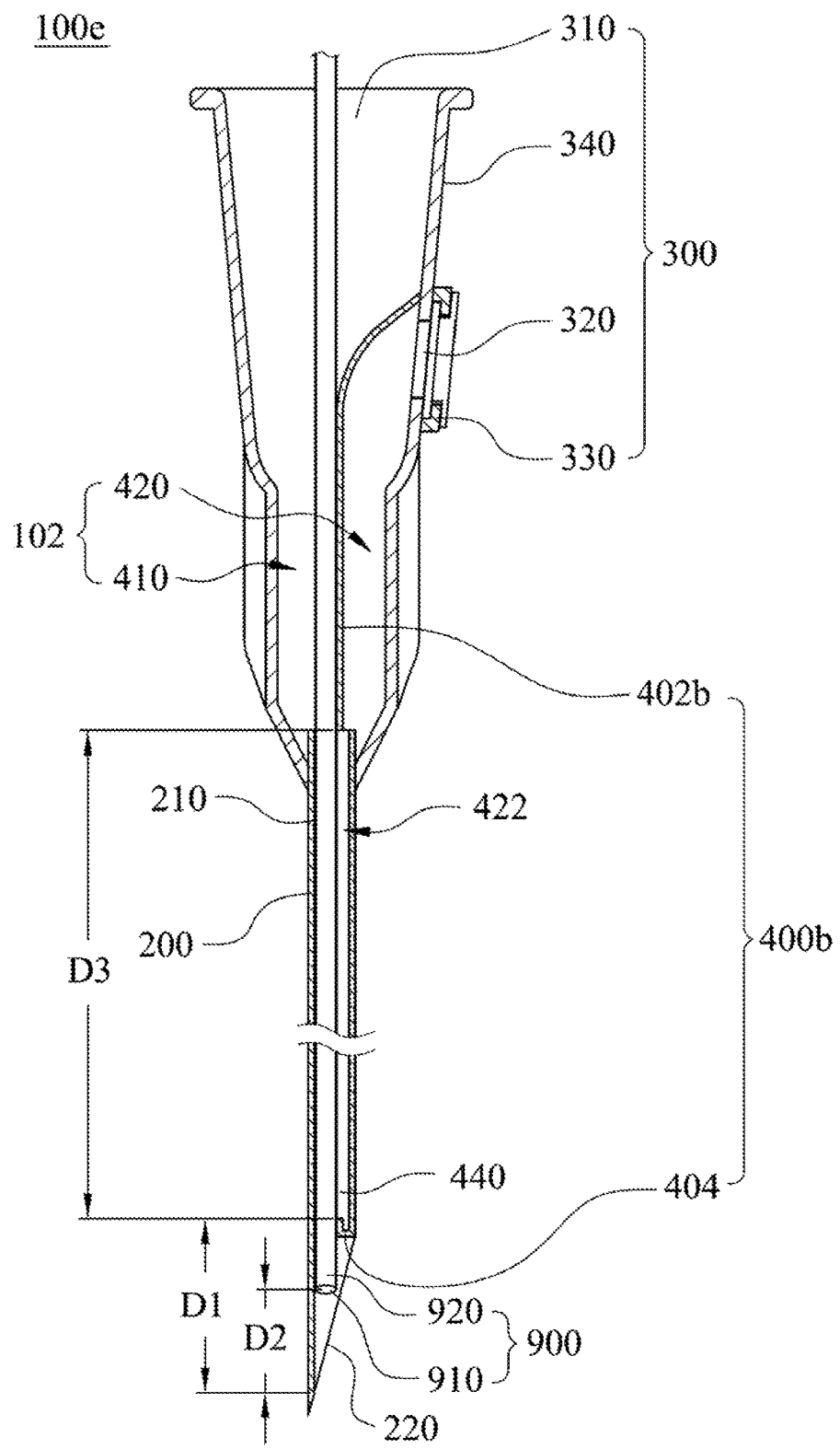
FIG. 11B shows a schematic view of the needle structure for injecting the filler of FIG. 11A.

FIG. 11A shows a schematic view of a needle structure 100e for monitoring the blood backflow situation according to further another embodiment of the present disclosure; and FIG. 11B shows a schematic view of the needle structure 100e for injecting the filler of FIG. 11A. The needle structure 100e includes a needle 200, a housing 300, a partitioning member 400b and a tube 900. In FIGS. 11A and 11B, the detail of the needle 200, the housing 300 and the tube 900 is the same as the embodiments of FIGS. 10A and 10B, and will not be described again herein. In FIGS. 11A and 11B, the needle structure 100e further includes the partitioning member 400b. The partitioning member 400b includes a first partitioning portion 402b, a second partitioning portion 404 and a blood backflow opening 440. The needle housing chamber 102 is separated into a first chamber 410 and a second chamber 420 by the partitioning member 400b. The blood backflow opening 440 has a diameter D3. The first partitioning portion 402b of FIG. 11A is shorter than the first partitioning portion 402a of FIG. 10A, so that the diameter D3 of the blood backflow opening 440 of the needle structure 100e of FIG. 11B is greater than the diameter D3 of the blood backflow opening 440 of the needle structure 100d of FIG. 10B. In other words, the first partitioning portion 402b is only disposed in the housing 300 and not disposed in the needle chamber 210 of the needle 200. The second partitioning portion 404 adjacent to the needle opening 220 is disposed in the needle chamber 210 of the needle 200. Hence, the needle 200 may be a thinner tube having a smaller diameter, thereby reducing a size of puncture wound caused by the needle 200. The operation of the needle structure 100e can be divided into two steps. The first step is for confirming the blood backflow situation, and the second step is for injecting the filler. In the first step, the injector penetrates the tube 900 through the first chamber 410 and the needle chamber 210, and moves the injection opening 910 to a first position, so that a second distance D2 between the injection opening 910 and the needle opening 220 is greater than a first distance D1 between the blood backflow opening 440 and the needle opening 220. An empty space 422 is formed between an outer wall of the tube 900 and an inner wall of the needle 200, and is one part of the second chamber 420. The empty space 422 is communicated with the needle opening 220 via the blood backflow opening 440, so that the injector can confirm whether or not the needle 200 is inserted into the blood vessel according to the blood backflow situation, as shown in FIG. 11A. In the second step, the injector pushes the tube 900 an interval toward the needle opening 220, so that the second distance D2 is smaller than the first distance D1. When the first distance D1 is greater than the second distance D2, the blood backflow opening 440 is closed by the tube wall 920 of the tube 900 so as to separate the empty space 422 from the needle opening 220, as shown in FIG. 11B. After that, the injector injects the filler contained in the tube 900 to the needle opening 220 and then extracts the tube 900 from the needle 200 and the first chamber 410 to complete the injection process. The needle structure 100e can prevent the filler into the empty space 422 from plugging, thus decreasing the difficulty of cleaning, reducing the weight and the diameter of the needle 200, enhancing the convenience of operation and increasing the operation safety.

Figure 12A:
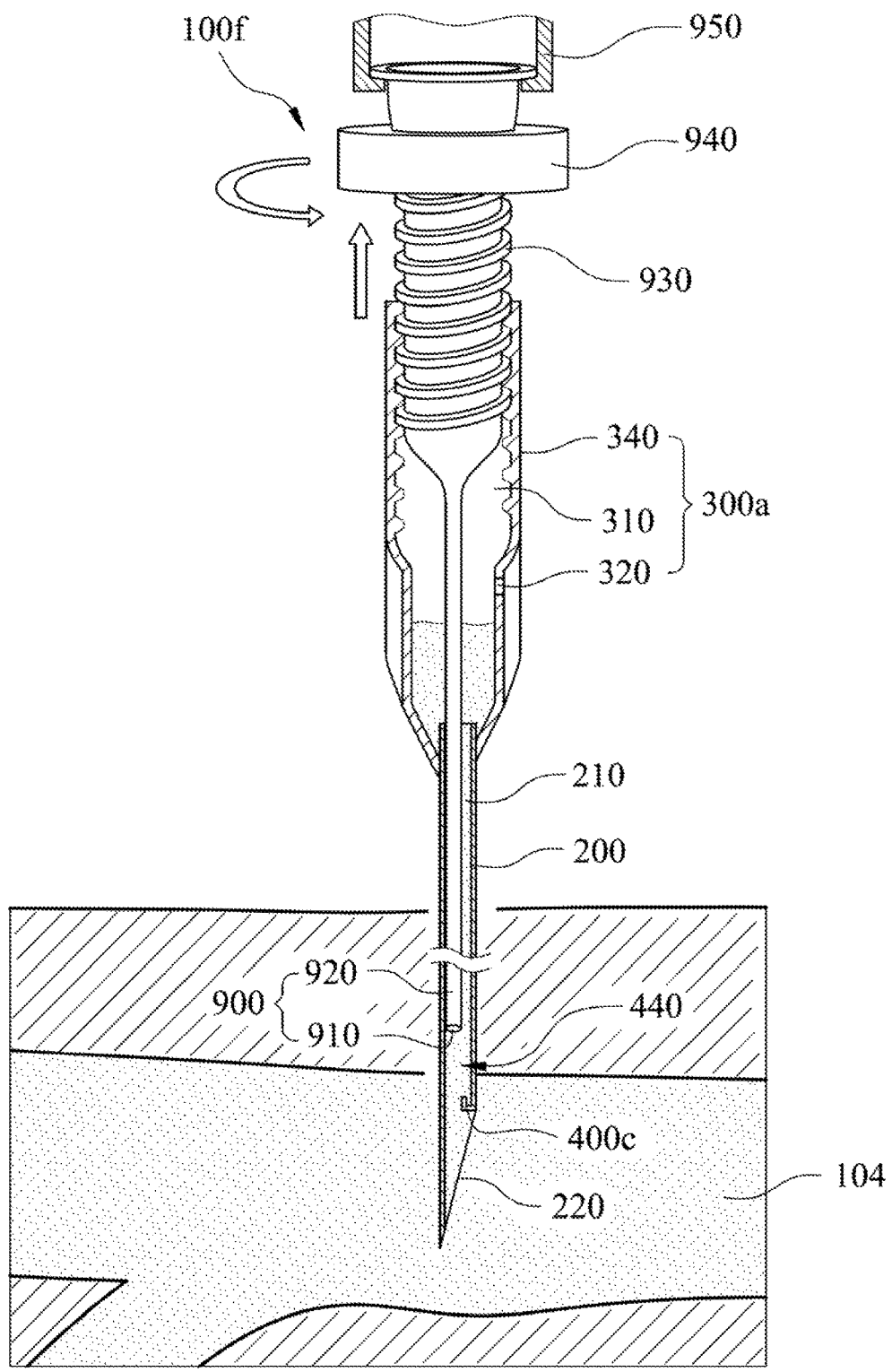
FIG. 12A shows a schematic view of a needle structure for inserting into a blood vessel according to still further another embodiment of the present disclosure.
Figure 12B:
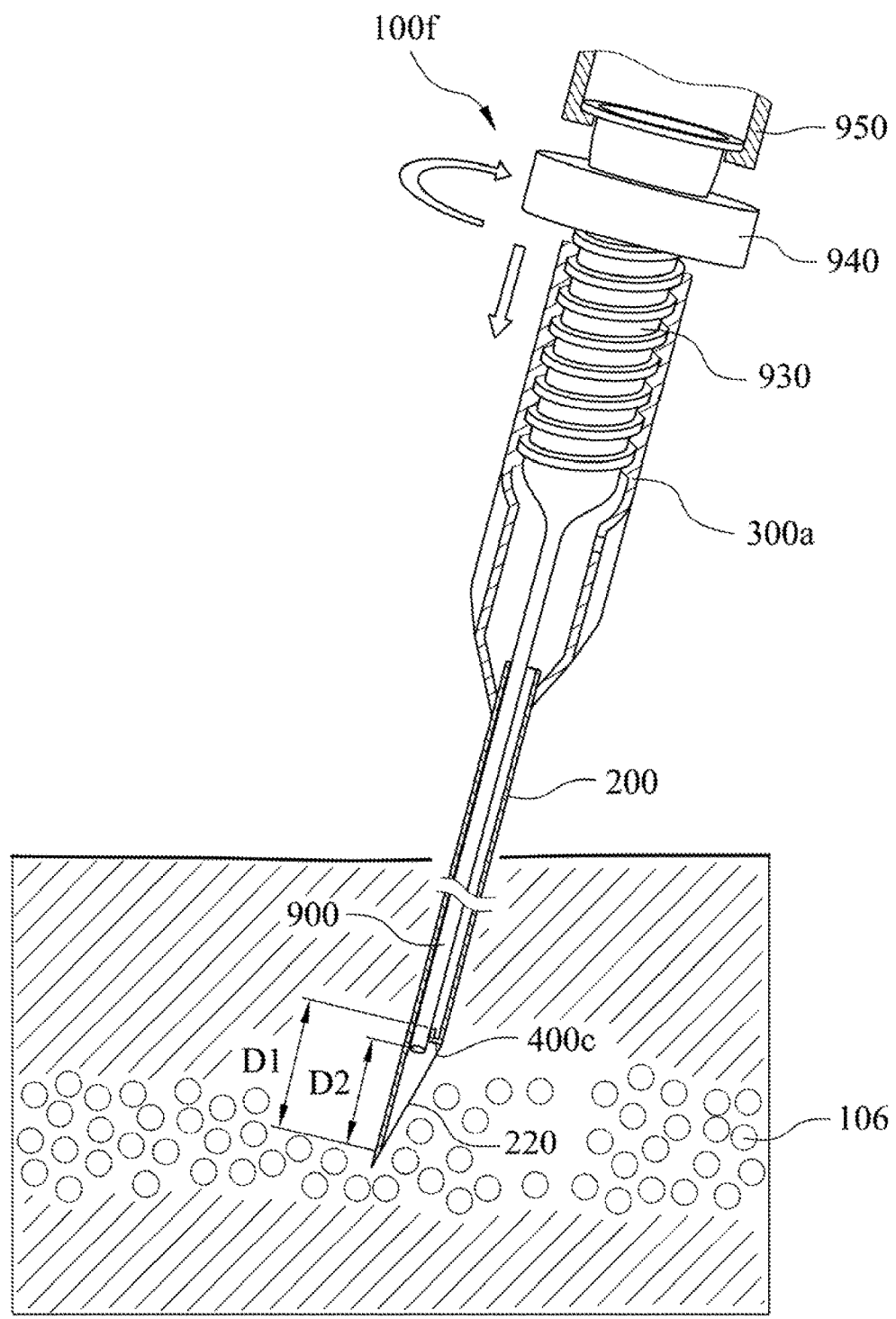
FIG. 12B shows a schematic view of the needle structure of FIG. 12A for injecting the filler into a non-vascular tissue.

FIG. 12A shows a schematic view of a needle structure 100f for inserting into a blood vessel 104 according to still further another embodiment of the present disclosure; and FIG. 12B shows a schematic view of the needle structure 100f of FIG. 12A for injecting the filler into a non-vascular tissue 106. The needle structure 100f includes a needle 200, a housing 300a, a tube 900, a threaded portion 930, a rotating portion 940 and a syringe barrel 950. In FIG. 12A, the detail of the tube 900 is the same as the detail of the tube 900 of FIG. 11A, and will not be described again herein. In FIGS. 12A and 12B, the needle 200 includes a needle chamber 210, a needle opening 220 and a partitioning member 400c. The needle opening 220 is connected to the needle chamber 210. The partitioning member 400c is disposed in the needle chamber 210. In addition, the needle structure 100f further includes the threaded portion 930, the rotating portion 940 and the syringe barrel 950, and the housing 300a includes a housing chamber 310, a housing opening 320 and a housing wall 340. The housing 300 is connected to the needle 200. The housing opening 320 is connected to the housing chamber 310 and disposed through the housing wall 340. The housing chamber 310 is connected to the needle chamber 210. There is no switch in the needle structure 100f, and the threaded portion 930 is connected between the tube 900 and one end of the rotating portion 940. The other end of the rotating portion 940 is connected to the syringe barrel 950. The tube 900, the threaded portion 930, the rotating portion 940 and the syringe barrel 950 are rotated synchronously when the rotating portion 940 is rotated by the injector, so that the second distance D2 between the injection opening 910 and the needle opening 220 can be adjusted by rotating the rotating portion 940. In FIG. 12A, the needle opening 220 of the needle 200 is inserted into the blood vessel, and the blood flows through the needle chamber 210 to the housing chamber 310. The injector can monitor the blood backflow situation via the housing 300 to know that the needle opening 220 is located in the blood vessel 104, and then the injector may stop the filler injection and change the injection position. In FIG. 12B, the needle 200 is inserted into the non-vascular tissue 106, and the rotating portion 940 is rotated by the injector for reducing the second distance D2. When the second distance D2 is smaller than the first distance D1 between the partitioning member 400c and the needle opening 220, the filler can be injected into the non-vascular tissue 106 by the injector, thus increasing the safety of surgery. In other words, when the first distance D1 between the partitioning member 400c and the needle opening 220 is smaller than the second distance D2 between the injection opening 910 and the needle opening 220, the partitioning member 400c and the tube wall 920 are separated to form a blood backflow opening 440. When the first distance D1 is greater than the second distance D2, the blood backflow opening 440 is closed by connecting the tube wall 920 to the partitioning member 400c.

Figure 13A:
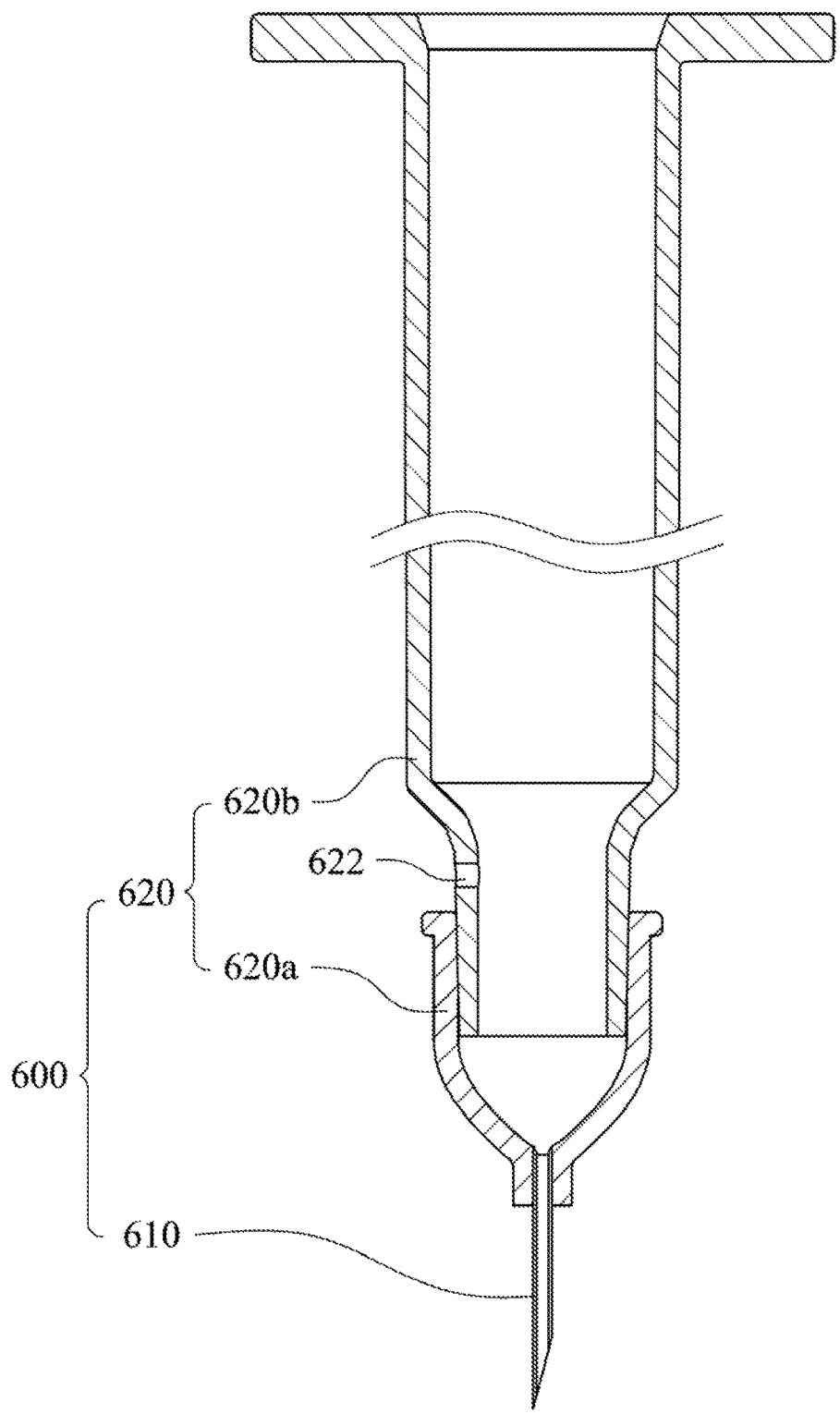
FIG. 13A shows a schematic view of an outer needle portion of a needle structure for inserting into the blood vessel according to another embodiment of the present disclosure.
Figure 13B:
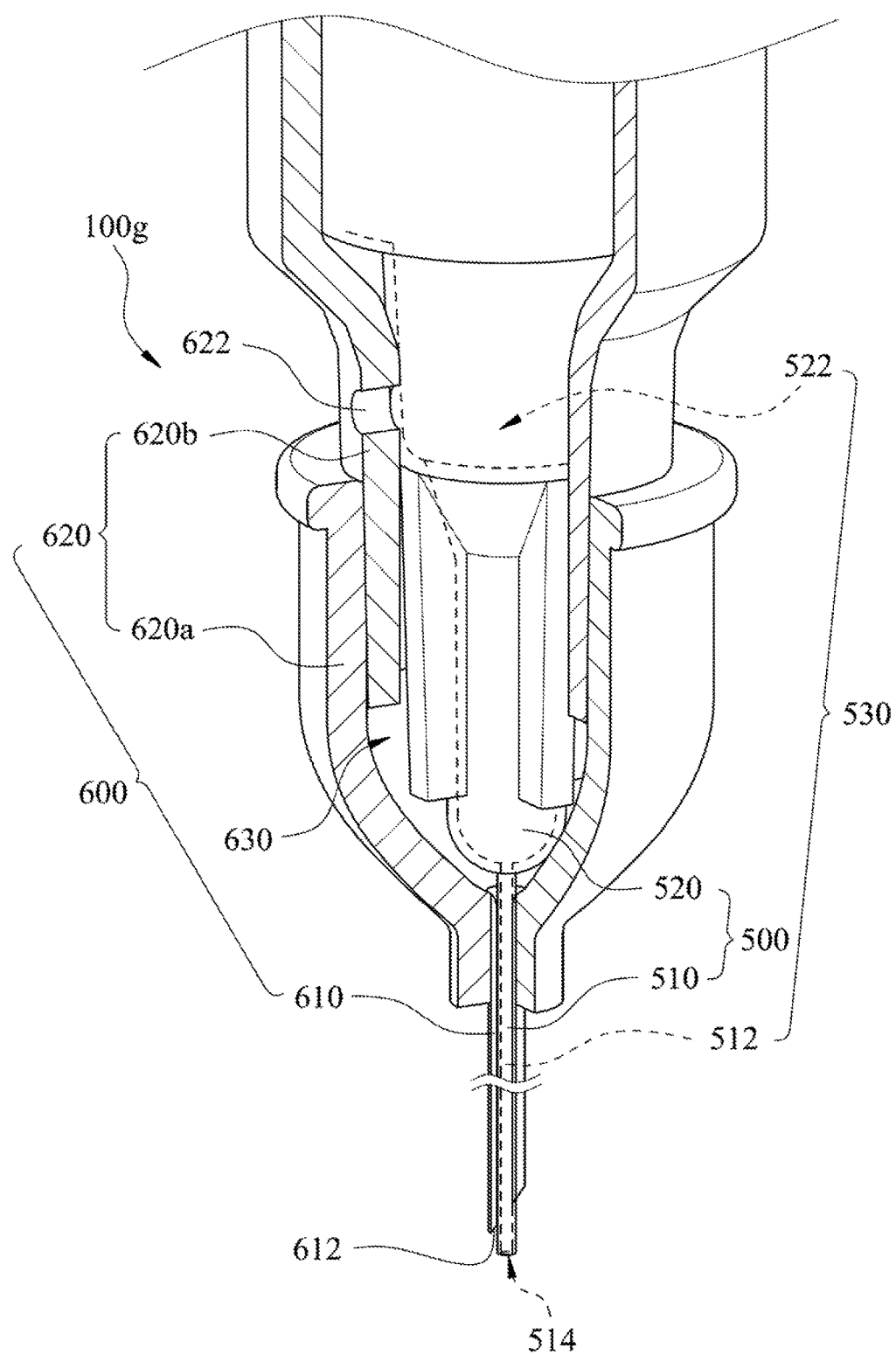
FIG. 13B shows a schematic view of the needle structure of FIG. 13A for injecting the filler into the non-vascular tissue.

FIG. 13A shows a schematic view of an outer needle portion 600 of a needle structure 100g for inserting into the blood vessel according to another embodiment of the present disclosure; and FIG. 13B shows a schematic view of the needle structure 100g of FIG. 13A for injecting the filler into the non-vascular tissue. The needle structure 100g for injecting the filler and monitoring the blood backflow situation simultaneously includes an inner needle portion 500 and an outer needle portion 600.

The inner needle portion 500 includes a first needle 510 and a first housing 520. The first needle 510 includes a needle chamber 512 and a needle opening 514 connected to the needle chamber 512. The first housing 520 is connected to the first needle 510. The first housing 520 includes a housing chamber 522 connected to the needle chamber 512 to form a first chamber 530, and the first chamber 530 is configured to contain the filler and is connected to the needle opening 514. In addition, the outer needle portion 600 is disposed around an outside of the inner needle portion 500. The outer needle portion 600 includes a second needle 610, a second housing 620 and a housing opening 622. The second needle 610 is disposed around an outside of the first needle 510 and has a blood backflow opening 612. The second housing 620 is disposed around an outside of the first housing 520. The second housing 620 includes a proximal portion 620a and a distal portion 620b. The proximal portion 620a has two ends connected to the second needle 610 and the distal portion 620b, respectively. A front end of the distal portion 620b is engaged into the proximal portion 620a. The housing opening 622 is disposed on the distal portion 620b. The inner needle portion 500 is movably positioned in the proximal portion 620a and the distal portion 620b. Moreover, a second chamber 630 is formed between the inner needle portion 500 and the outer needle portion 600 when the inner needle portion 500 is inserted into the outer needle portion 600. The first chamber 530 and the second chamber 630 are separated from each other. In FIG. 13A, there is no switch disposed on the second housing 620, and the second housing 620 is made of hard plastic which may be transparent or semi-transparent. The housing opening 622 is communicated with the blood backflow opening 612 via the proximal portion 620a and the second needle 610, so that the injector can confirm whether the second needle 610 of the outer needle portion 600 is inserted into the blood vessel or not according to the blood backflow situation. On the contrary, when the first needle 510 is inserted into the second needle 610, the injector can inject the filler disposed in the inner needle portion 500 to the needle opening 514, as shown in FIG. 13B. Therefore, the needle structure 100g of the present disclosure can prevent the filler into the blood vessel from blood clotting and increase the safety of surgery.

Figure 13C:
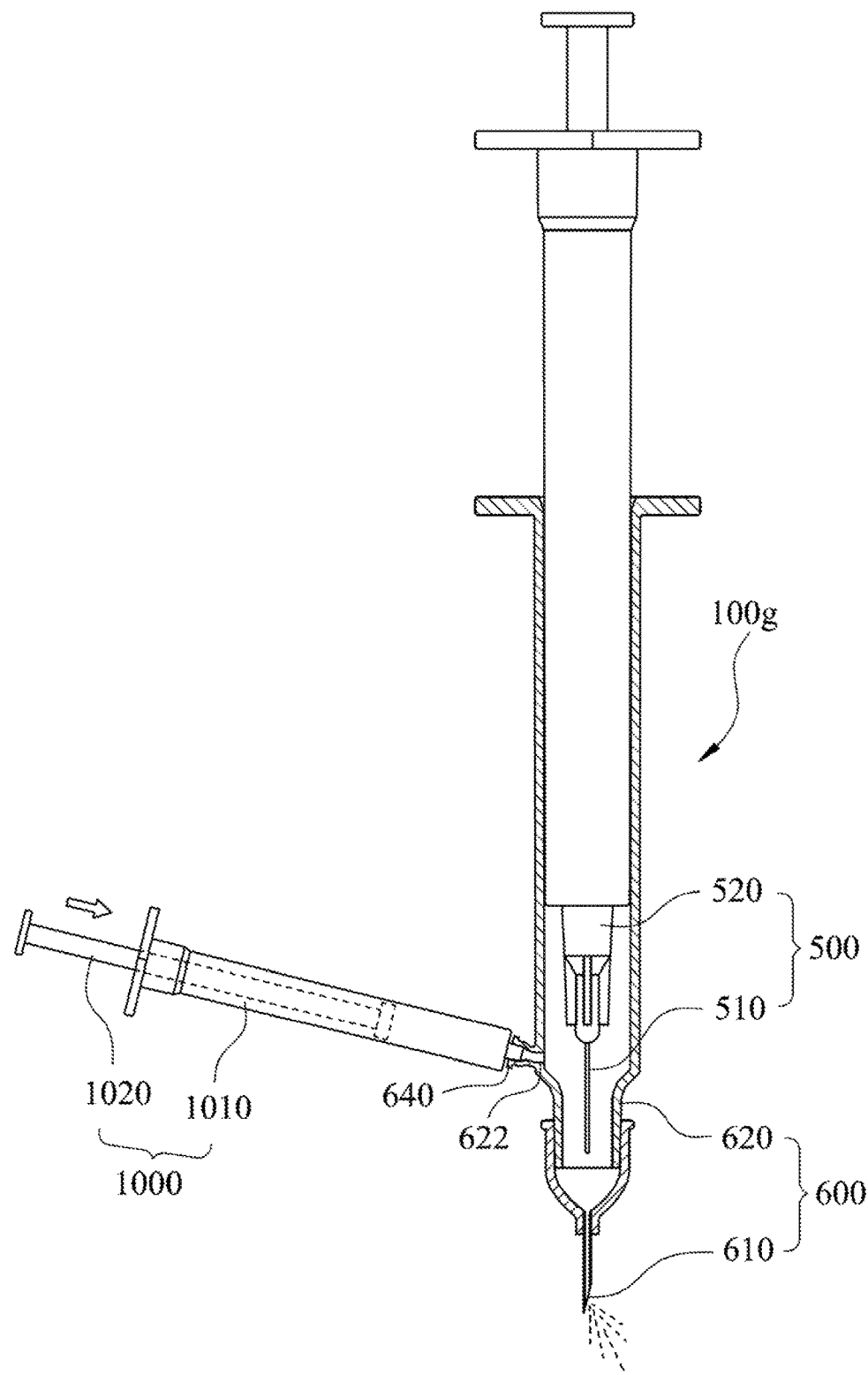
FIG. 13C shows a schematic view of the needle structure of FIG. 13A connected to a syringe assembly.

FIG. 13C shows a schematic view of the needle structure 100g of FIG. 13A connected to a syringe assembly 1000. In FIG. 13C, the detail of the inner needle portion 500, the second needle 610, the second housing 620 and the housing opening 622 is the same as the embodiments of FIG. 13A and FIG. 13B, and will not be described again herein. The outer needle portion 600 further includes a connecting seat 640 and a syringe assembly 1000. The connecting seat 640 is communicated with the housing opening 622 and integrally connected to the second housing 620. The connecting seat 640 is made of hard plastic and can be used to connect with various other types of syringe assemblies so as to remove the residual blood, discharge air or generate negative pressure via the syringe assembly 1000. The syringe assembly 1000 is connected to the connecting seat 640. In other words, when the syringe assembly 1000 is engaged with the connecting seat 640, the syringe assembly 1000 is communicated with the outer needle portion 600 via the connecting seat 640. The syringe assembly 1000 includes a syringe housing 1010 and a syringe handle 1020. The syringe housing 1010 is connected to the connecting seat 640. The syringe handle 1020 is disposed in the syringe housing 1010 and movably positioned in the syringe housing 1010. The syringe assembly 1000 is used for providing irrigation through the second needle 610 when the syringe handle 1020 is pushed. Accordingly, the residual blood can be removed from the second needle 610 by the syringe assembly 1000, and the outer needle portion 600 may be utilized for the next injection process so as to reduce the manufacturing cost.

According to the aforementioned embodiments and examples, the advantages of the present disclosure are described as follows.

1. The needle structure of the present disclosure utilizes the principles of the capillary phenomenon and the blood pressure inside the blood vessel to confirm whether or not the needle is inserted into the blood vessel without the operation of blood-sucking.

2. The needle structure of the present disclosure has the first chamber and the second chamber disconnected to the first chamber. The first chamber is configured to contain the filler. The second chamber is transparent, and the housing has the housing opening for confirming the blood backflow situation. When the housing opening is opened, the housing can be used to check the blood backflow situation. When the housing opening is closed, the filler is not entered into the second chamber, thereby preventing the filler into the blood vessel from blood clotting and increasing the safety of surgery.

3. The needle structure of the present disclosure not only can confirm the blood backflow situation without the operation of blood-sucking to increasing the safety of surgery, but also can improve the convenience of operation, thereby accomplishing the injection process successfully.

4. The needle structure of the present disclosure uses the double chambers and the partitioning member to inject the filler and monitor the blood backflow situation simultaneously so as to prevent the filler from being injected into blood vessels.

5. The needle structure of the present disclosure not only can greatly reduce the occurrence of side effects and accidents, but also can decrease the difficulty of cleaning and reduce the weight and the diameter of the needle.

6. The needle structure of the present disclosure can remove the residual blood from the second needle by the syringe assembly, and the outer needle portion may be reused to reduce the manufacturing cost.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A needle structure for injecting a filler and monitoring a blood backflow situation simultaneously, comprising:
   an inner needle portion, comprising:
      a first needle comprising a needle chamber and a needle opening connected to the needle chamber; and
      a first housing connected to the first needle, wherein the first housing comprises a housing chamber connected to the needle chamber to form a first chamber, and the first chamber is configured to contain the filler and is connected to the needle opening; and
   an outer needle portion disposed around an outside of the inner needle portion, wherein the outer needle portion comprises a housing opening and a blood backflow opening, a second chamber is formed between the inner needle portion and the outer needle portion, and the first chamber and the second chamber are separated from each other;
   wherein the outer needle portion further comprises:
      a second needle, wherein when the first needle is inserted into the second needle, the second needle is disposed around an outside of the first needle, and the blood backflow opening is disposed on the second needle; and
      a second housing connected to the second needle and disposed around an outside of the first housing, wherein the housing opening is disposed on the second housing;
      wherein the second housing is made of transparent or semi-transparent material;
   wherein the second housing comprises:
      a proximal portion having two ends, and one end of the proximal portion connected to the second needle; and
      a distal portion connected to the other end of the proximal portion, and the housing opening disposed on the distal portion;
   wherein the inner needle portion is movably positioned in the proximal portion and the distal portion, when the first needle is located away from the second needle, the housing opening is communicated with the blood backflow opening via the proximal portion and the second needle, and the second housing is configured to confirm whether the second needle of the outer needle portion is inserted into the blood vessel or not according to the blood backflow situation;
   wherein the filler is hyaluronic acid, calcium hydroxyapatite, polycaprolactone (PCL), collagen, poly-L-lactic acid (PLLA), fat, polyacrylamide (PAM), triamcinolone acetonide or lidocaine.

2. The needle structure of claim 1, wherein the second needle is a blunt needle or a sharp needle.

3. The needle structure of claim 1, wherein the outer needle portion further comprises:
   a connecting seat communicated with the housing opening and connected to the second housing; and
   a syringe assembly connected to the connecting seat, and the syringe assembly comprising:
      a syringe housing connected to the connecting seat; and
      a syringe handle disposed in the syringe housing and movably positioned in the syringe housing for providing irrigation through the second needle when the syringe handle is pushed.

4. The needle structure of claim 1, wherein the proximal portion has an inner surface and an outer surface, a front end of the distal portion is disposed within the proximal portion to be engaged with a part of the inner surface of the proximal portion, and the distal portion is separated from the outer surface of the proximal portion.

5. The needle structure of claim 1, wherein both the first housing and the first needle of the inner needle portion are movably positioned within both the proximal portion and the distal portion of the second housing of the outer needle portion.

* * * * *